(12) United States Patent  
Akhlaghpour

(10) Patent No.: US 11,883,112 B2
(45) Date of Patent: Jan. 30, 2024

(54) ROLLABLE DIGITIZER FOR COMPUTER-ASSISTED SURGERY

(71) Applicant: THINK SURGICAL, INC., Fremont, CA (US)

(72) Inventor: Hosna Akhlaghpour, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 705 days.

(21) Appl. No.: 17/046,910

(22) PCT Filed: Apr. 11, 2019

(86) PCT No.: PCT/US2019/027058
§ 371 (c)(1),
(2) Date: Oct. 12, 2020

(87) PCT Pub. No.: WO2019/200154
PCT Pub. Date: Oct. 17, 2019

(65) Prior Publication Data
US 2021/0145524 A1    May 20, 2021

Related U.S. Application Data

(60) Provisional application No. 62/657,658, filed on Apr. 13, 2018.

(51) Int. Cl.
*A61B 34/20*    (2016.01)
*A61B 34/30*    (2016.01)
(Continued)

(52) U.S. Cl.
CPC .............. *A61B 34/20* (2016.02); *A61B 34/30* (2016.02); *A61B 17/3472* (2013.01);
(Continued)

(58) Field of Classification Search
CPC ......... A61B 34/20; A61B 34/25; A61B 34/30; A61B 5/1077
See application file for complete search history.

(56) References Cited

U.S. PATENT DOCUMENTS 4,760,851 A * 8/1988 Fraser .................... G01B 5/004
600/587
6,033,415 A    3/2000 Mittelstadt et al.
(Continued)

OTHER PUBLICATIONS

Int'l Search Report for PCT/US2019/027058, dated Aug. 2, 2019.

*Primary Examiner* — Si Ming Ku
(74) *Attorney, Agent, or Firm* — MaxGoLaw PLLC

(57) ABSTRACT

A rollable digitizer device for collecting a plurality of points on a bone that includes a wheel having multiple probes emanating circumferentially therefrom. One or more contact sensors adapted to detect if at least one of probes is in contact with the bone. The contact sensors located in the wheel, on the wheel, proximal to said one or more contact sensors, or a combination thereof. A handle connected to the wheel and adapted to permit a user to roll the probes along the bone, so each of the probes make sequential and detectable contact with the bone to facilitate the collection of multiple points on the bone. A method for collecting a multiple registration points on a bone with the rollable digitizer device includes wielding the rollable digitizer by the handle. The probes are rolled along the surface of the bone to collect the plurality of registration points.

20 Claims, 5 Drawing Sheets

(51) Int. Cl.
    *A61B 90/00*     (2016.01)
    *A61B 90/50*     (2016.01)
    *A61B 17/34*     (2006.01)
    *A61B 17/00*     (2006.01)

(52) U.S. Cl.
    CPC ..... *A61B 90/50* (2016.02); *A61B 2017/00221* (2013.01); *A61B 2034/2059* (2016.02); *A61B 2034/2072* (2016.02); *A61B 2090/065* (2016.02); *A61B 2090/363* (2016.02); *A61B 2090/3945* (2016.02); *A61B 2090/3975* (2016.02)

(56) References Cited

U.S. PATENT DOCUMENTS

| | | |
|---|---|---|
| 8,961,536 B2 | 2/2015 | Nikou et al. |
| 2017/0245945 A1 | 8/2017 | Zuhars et al. |
| 2017/0258532 A1 | 9/2017 | Shalayev et al. |

\* cited by examiner

ROLLABLE DIGITIZER FOR COMPUTER-ASSISTED SURGERY

RELATED APPLICATIONS

This application claims priority benefit of U.S. Provisional Application Ser. No. 62/657,658 filed 13 Apr. 2018; the contents of which are hereby incorporated by reference.

TECHNICAL FIELD

The present invention generally relates to the field of computer-assisted orthopedic surgery, and more particularly to a rollable digitizer for collecting a plurality of registration points on a bone to register the bone to a computer-assisted surgical system in a time-effective manner.

BACKGROUND

Computer-assisted orthopedic surgery is an expanding field having applications in total joint arthroplasty (TJA), bone fracture repair, maxillofacial reconstruction, and spinal reconstruction. For example, the TSOLUTION ONE® Surgical System (THINK Surgical, Inc., Fremont, CA) aids in the planning and execution of total hip arthroplasty (THA) and total knee arthroplasty (TKA). The TSOLUTION ONE® Surgical System includes: a pre-operative planning software program to permit a user to generate a surgical plan using based on an image data set of the patient's bone and computer-aided design (CAD) files of several implants; and an autonomous surgical robot that precisely mills the bone to receive an implant according to the surgical plan. In order for the computer-assisted surgical system to accurately prepare a bone, the bone needs to be registered to the surgical system. Registration determines the spatial position and orientation (POSE) of the bone relative to the coordinates of the surgical plan and/or surgical system.

Several registration procedures are known in the art, illustratively including pin-based, point-to-point, point-to-surface, laser scanning, image-free, and image registration, as described in U.S. Pat. Nos. 5,951,475, 6,033,415, 8,287,522, and 8,010,177. However, the tasks required to perform these registration procedures are tedious and time consuming. The most commonly used registration procedure relies on the manual collection of several points (i.e., point-to-point, point-to-surface) on the bone using a tracked digitizer probe where the surgeon is instructed to collect several points on the bone that are readily mapped to corresponding points or surfaces on a representation of the bone (e.g., a 3-D bone model). Another registration procedure is image free registration, where several points on the bone are collected to directly create a three-dimensional model of the bone, a surface map of the bone, and/or a point cloud of the bone. This can require the collection of fifty or more points on the bone to create an accurate representation of the bone. In either case, collecting points on the bone is a time consuming and tedious process, and since bone registration is required for computer-assisted surgeries, any device, system or method that can improve the registration process is highly advantageous for reducing overall operating times and costs.

Thus, there exists a need in the art for an improved device, system, and method to facilitate the collection of a plurality of registration points on a bone to register the bone to a computer-assisted surgical system in a time-effective manner.

SUMMARY OF THE INVENTION

A rollable digitizer device for collecting a plurality of points on a bone that includes a wheel having multiple probes emanating circumferentially therefrom. One or more contact sensors adapted to detect if at least one of probes is in contact with the bone. The contact sensors located in the wheel, on the wheel, proximal to said one or more contact sensors, or a combination thereof. A handle connected to the wheel and adapted to permit a user to roll the probes along the bone, so each of the probes make sequential and detectable contact with the bone to facilitate the collection of multiple points on the bone.

A method for collecting a multiple registration points on a bone with the rollable digitizer device includes wielding the rollable digitizer by the handle. The probes are rolled along the surface of the bone to collect the plurality of registration points.

BRIEF DESCRIPTION OF THE DRAWINGS

The present invention is further detailed with respect to the following drawings that are intended to show certain aspects of the present of invention, but should not be construed as limit on the practice of the invention, wherein.

DETAILED DESCRIPTION

Figure 1:
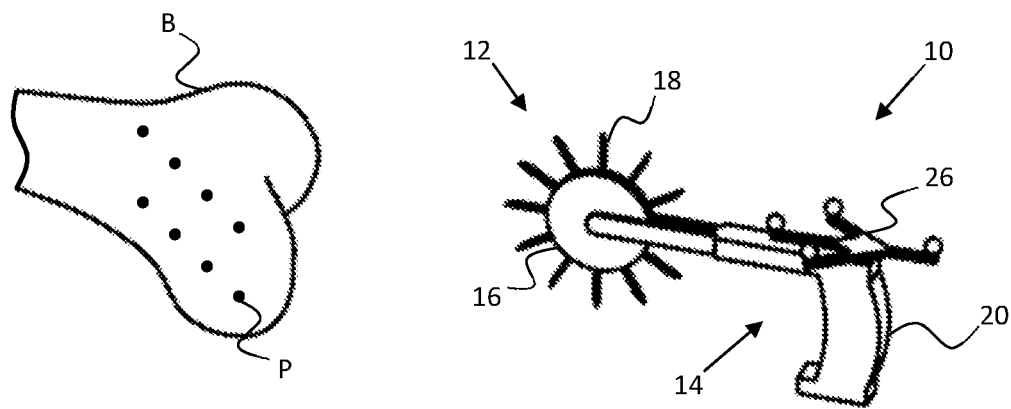
FIG. 1 depicts a rollable digitizer about to collect a plurality of points on a bone in accordance with embodiments of the invention.

The present invention has utility as a digitizer and method for collecting a plurality of registration points on a bone to register the bone to a computer-assisted surgical system in a time-effective manner. The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Further, it should be appreciated that although the systems and methods described herein make reference to the knee, the systems and methods may be applied to other bones and joints in the body illustratively including the hip, ankle, elbow, wrist, skull, and spine, as well as revision of initial repair or replacement of any of the aforementioned bones or joints.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "registration" refers to the determination of the spatial relationship between two or more objects and/or coordinate systems such as a computer-assist device, a bone, and/or an image data set of a bone. Illustrative methods of registration known in the art are described in U.S. Pat. Nos. 6,033,415; 8,010,177; 8,036,441; and 8,287,522; and U.S. Patent Application Publication 2016/0338776.

As used herein, the term "real-time" refers to the processing of input data within milliseconds such that calculated values are available within 10 seconds of computational initiation.

Also described herein is a 'computer-assisted surgical system'. A computer assisted surgical system refers to any system requiring a computer to aid in a surgical procedure. Examples of computer-assisted surgical systems include tracking systems, tracked passive instruments, active or semi-active hand-held surgical devices and systems, autonomous serial-chain manipulator systems, haptic serial chain manipulator systems, parallel robotic systems, or master-slave robotic systems, as described in U.S. Pat. Nos. 5,086,401; 7,206,626; 8,876,830; and 8,961,536; and 9,707,043; US Patent Application Publication US2017/0258532.

Figure 2:
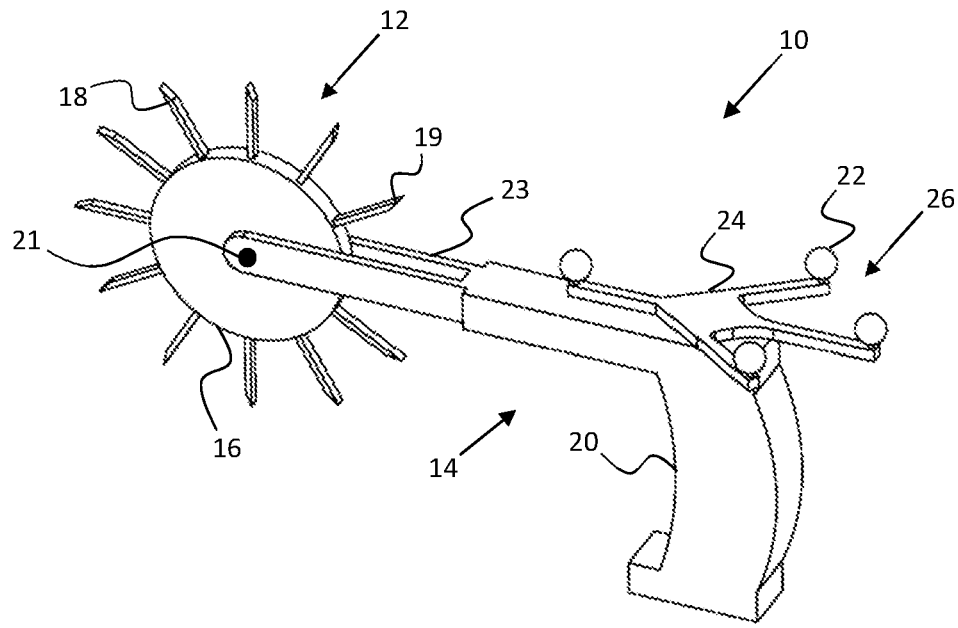
FIG. 2 depicts a perspective view of an optically tracked rollable digitizer in accordance with embodiments of the invention.
Figure 3:
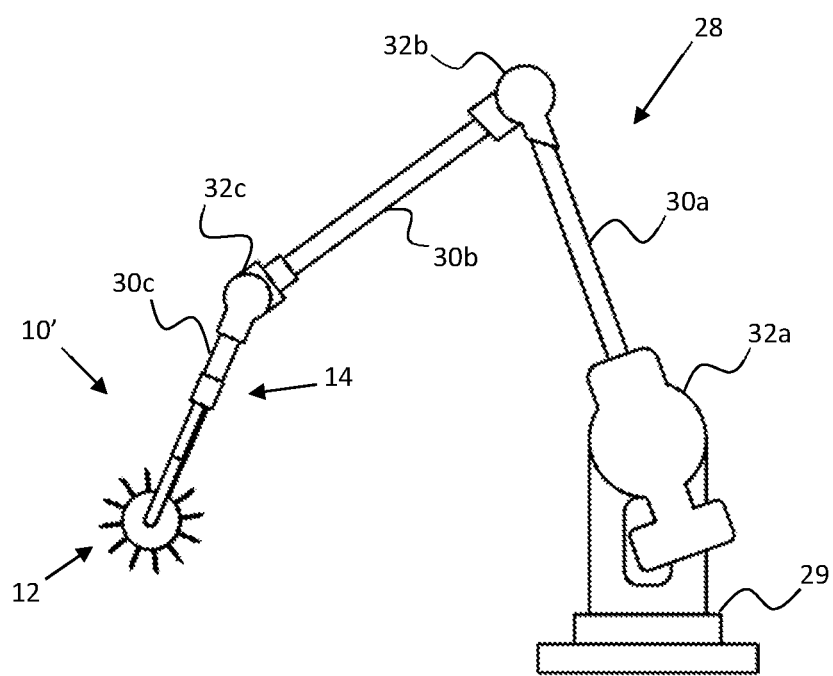
FIG. 3 depicts an elevation view of a mechanically tracked rollable digitizer in accordance with embodiments of the invention.

With reference now to the figures, FIGS. 1-5 depict specific inventive embodiments of a rollable digitizer 10. The rollable digitizer 10 generally includes a rollable portion 12 and a handle portion 14. The rollable portion 12 includes a wheel 16 having a plurality of probes 18 emanating circumferentially therefrom. The handle portion 14 includes a handle 20 pivotally connected to the wheel 16 at a pivot point concentric with and corresponding to a pivot pin or axle 21 to permit a user to roll the plurality of probes 18 along a bone B, wherein each of said plurality of probes 18 make sequential and detectable contact with the bone B to facilitate the collection of a plurality of points P on the bone B. As shown in FIG. 2 in greater detail, the handle portion 14 further includes a fork 23 projecting from the handle 20, where the fork 23 connects to both sides of the wheel 16 by the pivot pin or axle 21. The wheel 16 is in the form of a disc, cylinder, cube, or cuboid. In specific inventive embodiments, the wheel 16 is in the form of a disc, where the plurality of probes 18 emanate in a single row about the circumference of the wheel 16. The plurality of probes 18 may be spaced along the outer circumference of the wheel 16 in equal increments ranging from 5 to 60 degrees apart, which dictates the number of probes 18 emanating from the wheel 16; however, it should be appreciated that the number of probes 18 and spacing may vary depending on the spatial resolution of the points needed for collection. If the wheel 16 is in the form of a cylinder, cube, or cuboid, then the plurality of probes 18 may be arranged in various rows, intervals, or positions about the rolling surface of the wheel 16.

Each of the plurality of probes 18 further include a tip 19. In specific inventive embodiments, the tips 19 are configured to pierce through a layer of cartilage to make contact directly with the bone. The tips 19 may take the form of a needle point, bevel, or the like. Direct contact with the bone by the tip(s) 19 is required when registering a bone to an image data set of the bone, since the image data set of the bone is segmented to the outline of the bone. Therefore, if the tips 19 fail to pierce the cartilage, the collected points will be shifted by the thickness of the cartilage which may affect registration accuracy.

The rollable digitizer 10 further includes a tracking member 26 to permit a computer-assisted surgical system to determine, in real-time, the position and orientation (POSE) of the rollable digitizer 10 in physical space. In one embodiment, with reference particularly to FIGS. 1-2, the tracking member 26 is a plurality of fiducial markers 22 rigidly attached or integrated with the rollable digitizer 10. For example, the plurality of fiducial markers 22 may be arranged on a rigid body 24 that is rigidly attached to the handle 20 of the rollable digitizer 10. Here, a plurality of fiducial markers 22 arranged on a rigid body 24 is collectively referred to as a tracking array 26. The fiducial markers may be active markers, illustratively including light emitting diodes (LEDs) or other electromagnetic emitting markers, passive reflective markers, a set of lines, characters, or shapes, acoustic markers, or equivalents thereof. In other inventive embodiments, with reference to FIG. 3, the tracking member is a passive mechanical arm 28. The passive mechanical arm 28 includes a base 29, a plurality of links (30a, 30b, 30c), and a plurality of joints (32a, 32b, 32c) connecting the plurality of links (30a, 30b, 30c). In a particular embodiment, the base 29 of the mechanical arm 28 is attached and/or integrated to a robotic system as described in U.S. Pat. No. 6,033,415 as a bone digitizer arm. The rollable digitizer 10' is assembled to a distal link 30c of the mechanical arm 28, where the POSE of the rollable digitizer 10' is determined in real-time based on the kinematic model of the mechanical arm 28 and output from one or more encoders disposed in the joints (32a, 32b, 32c). It should be appreciated, that the distal link 30c may act as the handle 20 of the rollable digitizer 10 to permit the user to wield the rollable digitizer 10 when assembled to the passive mechanical arm 28.

Figure 4:
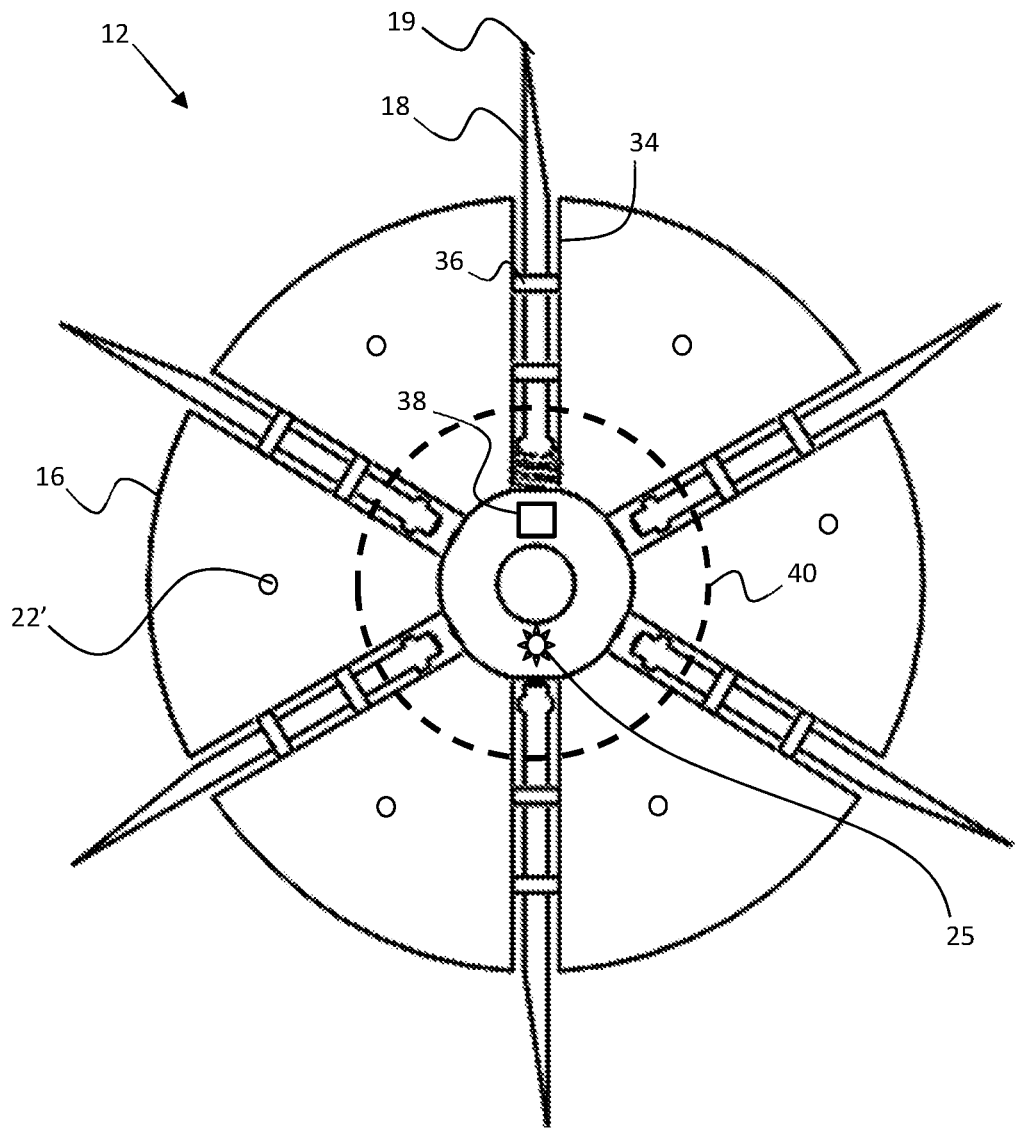
FIG. 4 depicts a cross-sectional view of a rollable portion of the rollable digitizer in accordance with embodiments of the invention.

Referring now to FIG. 4, a cross-section of the rollable portion 12 is shown. Each of the plurality of probes 18 reside in a channel 34 in the wheel 16, where the probes 18 can linearly translate and/or compress therein to an extent to permit one or more contact sensors to detect if a probe 18 is in contact with an external object (e.g., bone surface). The channels 34 may further include one or more brackets 36 that support/guide the probes 18 therein.

Embodiments of the rollable digitizer 10 may further include an encoder 38 or other sensor to track the position of each of the plurality of probes 18 relative to the tracking member. The sensor of the encoder 38 may be positioned on the wheel 16 and rotate with the wheel 16 while sensing marks or other indicia positioned on an inside surface of the fork 23 (the inside surface being a surface facing the wheel 16). In other inventive embodiments, the sensor of the encoder 38 is positioned on the inside surface of the fork 23 while sensing marks or other indicia on the face of the wheel 16. Alternatively, a plurality of fiducial markers 22' may be positioned directly on the wheel 16 where a tracking system can determine the orientation of the wheel 16 in real-time. By knowing the length of the probes 18, the geometric configuration of the probes 18 (e.g., angular spacing), the rotational position of the wheel as determined by the encoder 38/fiducial markers 22', and the POSE of the tracking member (unless the tracking member is a plurality of markers 22' directly on the wheel 16), then the POSE of each probe tip 19 is known in real-time. To determine which probe 18 is contacting the bone B to collect a point, the wheel 16 and/or probes 18 include one or more contact sensors as further described below.

Figure 5:
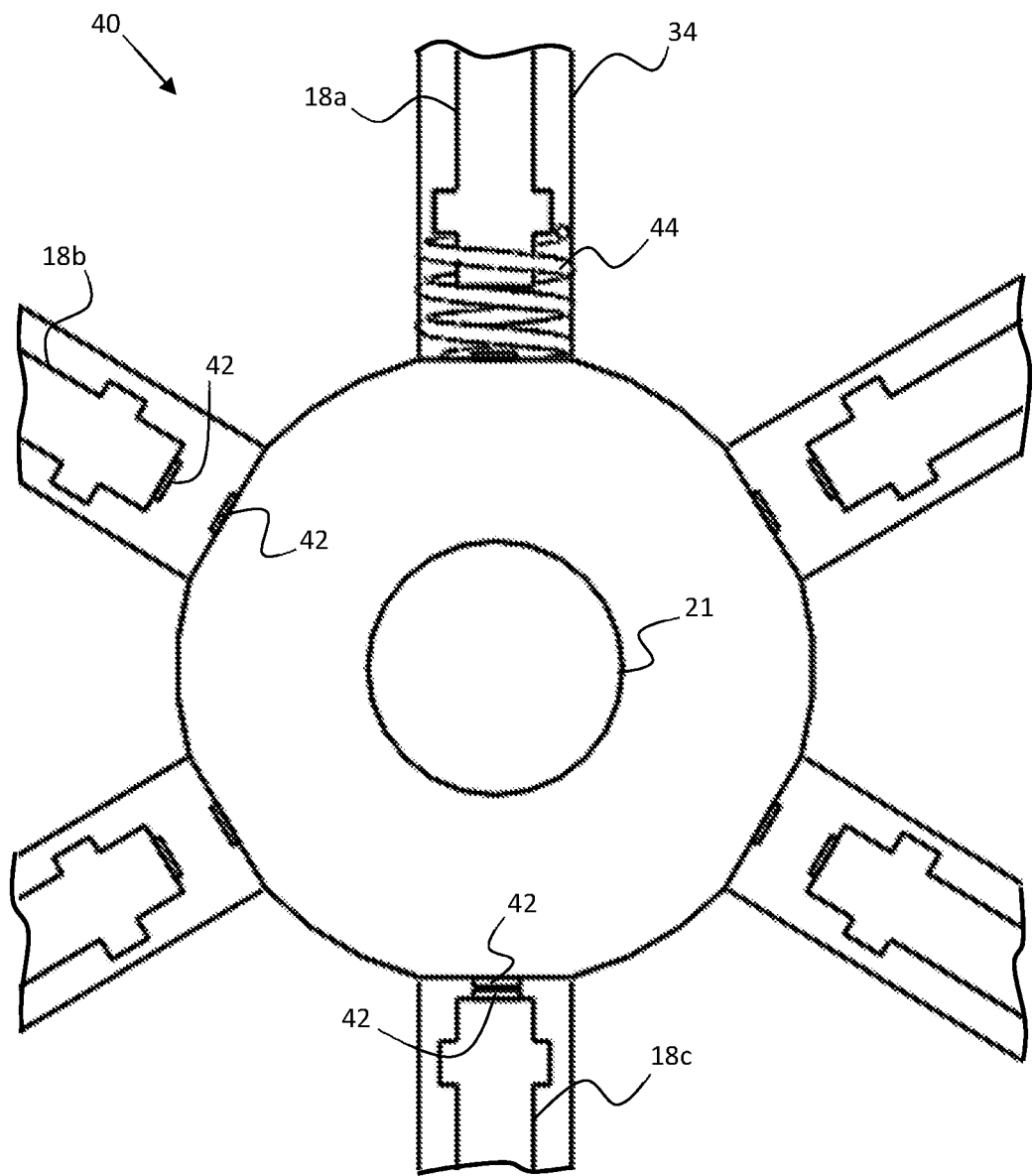
FIG. 5 depicts a detailed view of the region circled in FIG. 4 in accordance with embodiments of the invention.

FIG. 5 depicts a detailed view of the region inside the broken circle 40 of FIG. 4. The wheel 16 and/or probes (18*a*, 18*b*, 18*c* . . . ) include one or more contact sensors 42 to detect when a probe 18 contacts the surface of the bone B as the wheel 16 is being rolled. Once contact is detected, a registration point is collected where the POSE of the point is known in space based on the aforementioned tracking mechanisms. The contact sensors 42 may be, for example, strain gauges, piezoelectric sensors, speed sensors, displacements sensors, position sensors, optical sensors, electrical switch, and equivalents thereof, with the main criteria being the ability to detect contact of the probe 18 with an external object (e.g., bone surface). In some embodiments, the contact sensor 42 is positioned on a proximal end of the probe 18 and linearly translates/compresses to make contact with a proximal end of the channel 34. In other embodiments, the contact sensor 42 is positioned at the proximal end of the channel 34, where the probe 18 translates/compresses and makes contact with the sensor 42. While in other embodiments, a first contact sensor 42 is positioned at a proximal end of the probe 18 and a second contact sensor 42 is positioned at a proximal end of the channel 34, wherein upon contact an electrical circuit is formed to detect contact. Probe 18*c* depicts a probe in contact with the bone as the contact sensors 42 are in contact with each other, while the other probes are in a non-contact state. Each channel 34 may further include a biasing spring 44 disposed therein to reset the position of the probe 18 into a non-contact state when the probe 18 is no longer contacting an external object.

The rollable digitizer 10 may further include an LED 25 (as best seen in FIG. 2) for transmitting data generated by the encoder 38 and/or contact sensors 42 to the computer-assisted surgical system as described in U.S. Patent Application Publication US20170245945 making the rollable digitizer 10 completely wireless for use. In other embodiments, electrical wiring between the LED 25, encoder 38, and/or contact sensors 42 may be wired through the fork 23 and handle 20 to the computer-assisted surgical system to transfer the data generated from the encoder 38 and/or contacts sensors 42.

A method for collecting a plurality of registration points with the rollable digitizer 10 includes the following. A user first wields the rollable digitizer 10 by the handle 20 and rolls the plurality of probes 18 along the surface of the bone B. As the probes make contact with the bone B, data from the encoder 38, contact sensors 42, and tracking member 26 is sent to the computer-assisted surgical system to determine the POSE of each collected point on the bone. The points are then either mapped to corresponding points on a representation of the bone (e.g., bone model), or the points are used directly to generate a point cloud, surface map, or bone representation directly. The bone is successfully registered once the points are accurately mapped or enough points have been collected to generate a sufficient point cloud, surface map, or bone representation.

Surgical System

Figure 6:
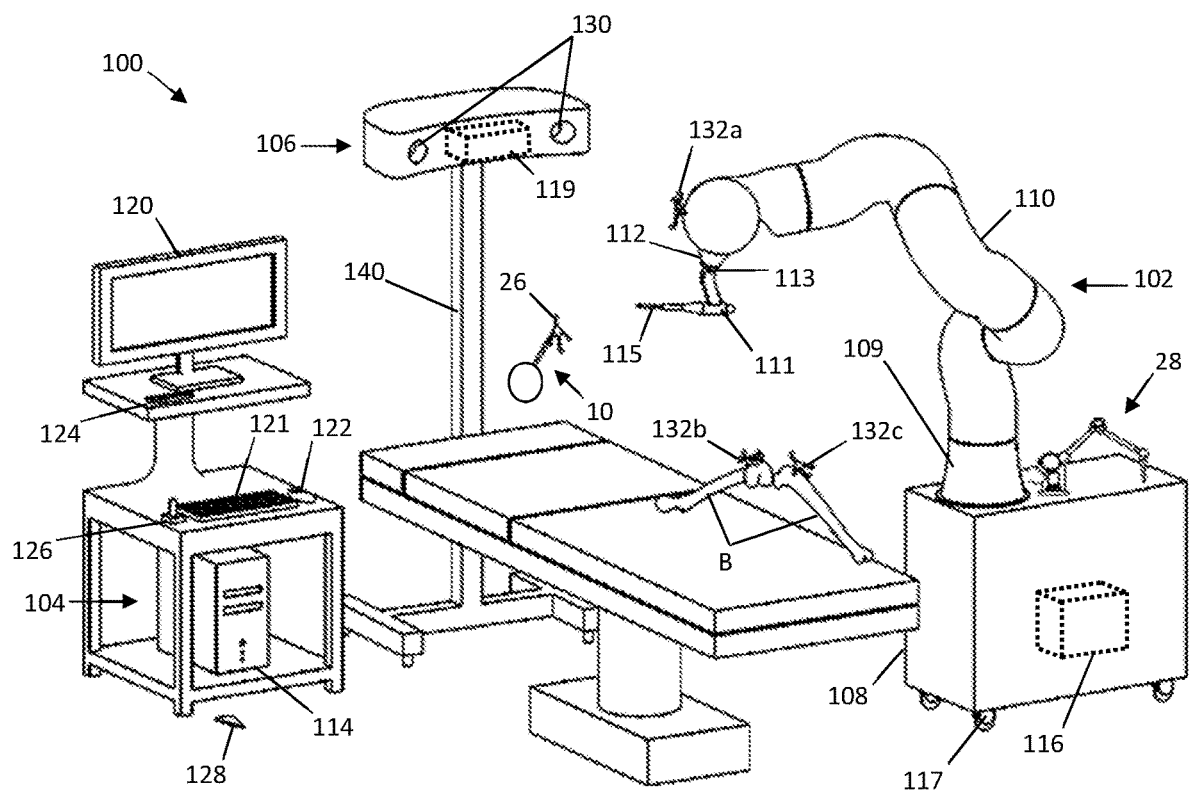
FIG. 6 depicts a surgical system in which the rollable digitizer is implemented in accordance with embodiments of the invention.

With reference to FIG. 6, an example of a computer-assisted surgical system 100 in the context of an operating room (OR) is shown. The surgical system 100 generally includes a surgical robot 102, a computing system 104, a mechanical arm 28 and/or a non-mechanical tracking system 106 (e.g., an optical tracking system, an electro-magnetic tracking system), and the rollable digitizer 10.

The surgical robot 102 may include a movable base 108, a manipulator arm 110 connected to the base 108, an end-effector flange 112 located at a distal end of the manipulator arm 110, and an end-effector assembly 111 removably attached to the flange 112 by way of an end-effector mount/coupler 113. The end-effector assembly 111 holds and/or operates an end-effector tool 115 that interacts with a portion of a patient's anatomy. The base 108 includes a set of wheels 117 to maneuver the base 108, which may be fixed into position using a braking mechanism such as a hydraulic brake. The base 108 may further include an actuator 109 to adjust the height of the manipulator arm 110. The manipulator arm 110 includes various joints and links to manipulate the tool 115 in various degrees of freedom. The joints are illustratively prismatic, revolute, spherical, or a combination thereof.

The computing system 104 generally includes a planning computer 114; a device computer 116; an optional tracking computer 119 if a tracking system 106 is present; and peripheral devices. The planning computer 114, device computer 116, and tracking computer 119, may be separate entities, single units, or combinations thereof depending on the surgical system. The peripheral devices allow a user to interface with the robotic surgical system 100 and may include: one or more user-interfaces, such as a display or monitor 120; and user-input mechanisms, such as a keyboard 121, mouse 122, pendent 124, joystick 126, foot pedal 128, or the monitor 120 in some inventive embodiments may have touchscreen capabilities.

The planning computer 114 contains hardware (e.g., processors, controllers, and memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan includes operational data for modifying a volume of tissue that is defined relative to the anatomy, such as a set of points in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue. The data generated from the planning computer 114 may be transferred to the device computer 116 and/or tracking computer 136 through a wired or wireless connection in the operating room (OR); or transferred via a non-transient data storage medium (e.g., a compact disc (CD), a portable universal serial bus (USB) drive).

The device computer 116 in some inventive embodiments is housed in the moveable base 108 and contains hardware (e.g., controllers), software, data and utilities that are preferably dedicated to the operation of the surgical robot 102. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, utilizing position and orientation (POSE) data from the tracking system 106, and reading data received from the mechanical arm 28.

The optional tracking system 106 of the surgical system 100 may be an optical tracking system as described in U.S. Pat. No. 6,061,644. The optical tracking system includes two or more optical receivers 130 to detect the position of tracking arrays (26, 132a, 132b, 132c), where each tracking array (26, 132a, 132b, 132c) has a unique arrangement of fiducial markers 22, or a unique transmitting wavelength/frequency if the markers 22 are active LEDs. The tracking system 106 may be built into a surgical light, located on a boom, a stand 140, or built into the walls or ceilings of the OR. The tracking system computer 136 may include tracking hardware, software, data and utilities to determine the POSE of objects (e.g., bones B, rollable digitizer 10, surgical robot 102) in a local or global coordinate frame. The POSE of the objects is collectively referred to herein as POSE data, where this POSE data may be communicated to the device computer 116 through a wired or wireless connection. Alternatively, the device computer 116 may determine the POSE data using the position of the fiducial markers detected from the optical receivers 130 directly.

The POSE data is used by the computing system 104 during the procedure to update the POSE and/or coordinate transforms of the bone B, the surgical plan, and the surgical robot 102 as the manipulator arm 110 and/or bone B move during the procedure, such that the surgical robot 102 can accurately execute the surgical plan. In another embodiment, the surgical system 100 does not include a tracking system 106, but instead employs a mechanical arm 28, and a bone fixation and monitoring system that fixes the bone directly to the surgical robot 102 and monitors bone movement as described in U.S. Pat. No. 5,086,401. The tracking system 106 and/or mechanical arm 28 further utilizes POSE data from the rollable digitizer 10 along with data from the encoder 38 and one or more contact sensors 42 to efficiently collect a plurality of registration points on the bone B as described above.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A rollable digitizer device for collecting a plurality of points on a bone, comprising:
    a wheel having a plurality of probes emanating circumferentially therefrom;
    one or more contact sensors adapted to detect if at least one of the plurality of probes is in contact with the bone, said one or more contact sensors located in said wheel, on said wheel, proximal to said one or more probes of the plurality of probes, or a combination thereof; and
    a handle connected to said wheel and adapted to permit a user to roll the plurality of probes along the bone, wherein each of said plurality of probes make sequential and detectable contact with the bone to facilitate the collection of a plurality of points on the bone.

2. The device of claim 1 wherein the handle further comprises a fork projecting from the handle, where the fork connects to said wheel with a pivot pin or axle.

3. The device of claim 1 wherein said wheel is in the form of a disc, cylinder, cube, or cuboid.

4. The device of claim 3 wherein said wheel is in the form of a disc, where the plurality of probes emanate in a single row about a circumference of said wheel.

5. The device of claim 4 wherein the plurality of probes are spaced along the outer circumference of said wheel in equal increments ranging from 5 to 60 degrees apart.

6. The device of claim 1 wherein the plurality of probes further comprise a tip configured to pierce through a layer of cartilage to make contact directly with the bone.

7. The device of claim 1 further comprising a tracking member to permit a computer-assisted surgical system to determine, in real-time, the position and orientation (POSE) of the rollable digitizer in physical space.

8. The device of claim 7 wherein the tracking member comprises a plurality of fiducial markers rigidly attached or integrated with the rollable digitizer.

9. The device of claim 8 wherein the plurality of fiducial markers are arranged as a tracking array.

10. The device of claim 8 wherein the fiducial markers are at least one of active markers including light emitting diodes (LEDs) or other electromagnetic emitting markers, or passive reflective markers.

11. The device of claim 7 wherein the tracking member is a passive mechanical arm.

12. The device of claim 11 wherein the passive mechanical arm further comprises a base in mechanical communication with a plurality of links, and a plurality of joints connecting the plurality of links.

13. The device of claim 12 wherein the rollable digitizer is assembled to a distal link of the plurality of links of the mechanical arm; and
    wherein the POSE of the rollable digitizer is determined in real-time based on a kinematic model of the mechanical arm and output from one or more encoders disposed in the plurality of joints.

14. The device of claim 1 wherein the plurality of probes reside in a corresponding plurality of separate channels in said wheel, where the plurality of probes linearly translate or compress within the channels to an extent to permit the one or more contact sensors to detect if a probe of the plurality of probes is in contact with the bone.

15. The device of claim 1 further comprising a sensor mounted to said wheel to track the position of each of the plurality of probes relative to a tracking member, where the sensor senses a set of marks or other indicia positioned on an inside surface of a fork projecting from the handle, where the fork connects to said wheel with a pivot pin or axle.

16. The device of claim 1 further comprising a transmitter light emitting diode (LED) that wirelessly transmits data generated by the one or more contact sensors to a computer-assisted surgical system.

17. A method for collecting a plurality of registration points on a bone with the rollable digitizer device of claim 1, the method comprising:
wielding the rollable digitizer by the handle and rolling the plurality of probes along the surface of the bone to collect the plurality of registration points.

18. The method of claim 17 further comprising:
determining the position of each collected registration point on the bone; and
mapping the plurality of registration points to a corresponding set of points on a model representation of the bone, or the plurality of registration points are used directly to generate a point cloud, surface map, or bone model representation directly.

19. A computer-assisted surgical system utilizing the rollable digitizer device of claim 1 for collecting a plurality of registration points on a bone for a surgical procedure, the system comprising:
a surgical robot;
a computing system;
a tracking system; and
wherein the collected plurality of registration points are used by the computing system to map the plurality of registration points to a corresponding set of points on a model representation of the bone, or the plurality of registration points are used directly to generate a point cloud, surface map, or bone model representation directly.

20. The system of claim 19 wherein the tracking system includes at least one of: a) a mechanical arm attached to the rollable digitizer; or b) an optical tracking system for tracking a plurality of fiducial markers attached to or integrated with the rollable digitizer.

* * * * *